United States Patent
Schmidt et al.

(10) Patent No.: US 9,528,059 B2
(45) Date of Patent: Dec. 27, 2016

(54) CATALYTIC PURIFICATION OF FATTY ACID ALKYL ESTERS USED IN FUELS

(75) Inventors: Stephen R. Schmidt, Silver Spring, MD (US); Meenakshi S. Krishnamoorthy, Columbia, MD (US); Manoj M. Koranne, Clarksville, MD (US); Heiko Morell, Rodgau (DE); Jochen G. Metzger, Worms (DE)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

(21) Appl. No.: 14/127,583

(22) PCT Filed: May 22, 2012

(86) PCT No.: PCT/US2012/038947
§ 371 (c)(1),
(2), (4) Date: Dec. 19, 2013

(87) PCT Pub. No.: WO2012/177348
PCT Pub. Date: Dec. 27, 2012

(65) Prior Publication Data
US 2014/0109466 A1   Apr. 24, 2014

Related U.S. Application Data

(60) Provisional application No. 61/594,730, filed on Feb. 3, 2012, provisional application No. 61/499,565, filed on Jun. 21, 2011.

(51) Int. Cl.
*C10L 1/19*    (2006.01)
*C11B 3/02*    (2006.01)
(Continued)

(52) U.S. Cl.
CPC ............... *C10L 1/19* (2013.01); *C07C 67/03* (2013.01); *C07C 67/60* (2013.01); *C10L 1/026* (2013.01);
(Continued)

(58) Field of Classification Search
None
See application file for complete search history.

(56) References Cited

U.S. PATENT DOCUMENTS

| | | | |
|---|---|---|---|
| 3,864,370 A | 2/1975 | Yamashita et al. | 260/419 |
| 4,371,470 A | 2/1983 | Matsukura et al. | 260/428 |

(Continued)

FOREIGN PATENT DOCUMENTS

| | | | |
|---|---|---|---|
| EP | 2042588 | 4/2009 | C11C 3/00 |
| WO | 2006050925 | 5/2006 | |

(Continued)

OTHER PUBLICATIONS

Rafaat, A.A., Biodiesel production using solid metal oxide catalysts, Dec. 1, 2010, Int. J. Enviorn. Sci. Tech, (8), (1), pp. 203-221.*

(Continued)

*Primary Examiner* — Yate K Cutliff
(74) *Attorney, Agent, or Firm* — Beverly J. Artale; Charles A. Cross

(57) ABSTRACT

The process of this invention removes impurities from transesterification products comprising primarily fatty acid alkyl esters (FAAE) that are being processed for final fuel products, such as biodiesel. The inventive process is catalytic, and the resulting ester is suitable for use as biodiesel. Metal oxide and mixed metal oxide catalysts are particularly suitable. The invention is particularly suitable for treating fatty acid alkyl ester compositions comprising impurities such as glycerin, sterol glycosides, and/or triglyceride, diglyceride and/or monoglyceride. The invention is particu- (Continued)

larly useful in treating FAAE transesterification products made using homogeneous alkali catalysts. The treated ester exhibits improved performance under cold weather conditions, which can be measured by methods such as ASTM 7501 Cold Soak Filtration Test (CSFT).

50 Claims, 4 Drawing Sheets

(51) Int. Cl.
  C10L 1/02 (2006.01)
  C11C 3/00 (2006.01)
  C07C 67/03 (2006.01)
  C07C 67/60 (2006.01)
(52) U.S. Cl.
  CPC ............... *C11B 3/02* (2013.01); *C11C 3/003* (2013.01); *Y02E 50/13* (2013.01)

(56) References Cited

U.S. PATENT DOCUMENTS

| | | | |
|---|---|---|---|
| 4,492,678 A | 1/1985 | Yoo et al. | 423/244 |
| 4,728,635 A | 3/1988 | Bhattacharyya | 502/304 |
| 5,908,946 A | 6/1999 | Stern et al. | 554/167 |
| 6,956,125 B2 | 10/2005 | Wollmann et al. | 552/545 |
| 7,420,073 B2 | 9/2008 | Hillion et al. | 554/174 |
| 7,635,398 B2 | 12/2009 | Bertram et al. | 44/605 |
| 7,851,643 B2 | 12/2010 | Hillion et al. | 554/167 |
| 2002/0058827 A1 | 5/2002 | Wollmann et al. | 552/545 |
| 2002/0082434 A1 | 6/2002 | Bonakdar et al. | 552/545 |
| 2005/0081436 A1 | 4/2005 | Bertram et al. | 44/605 |
| 2007/0066838 A1 | 3/2007 | Hillion et al. | 554/174 |
| 2007/0151146 A1* | 7/2007 | Lee et al. | 44/605 |
| 2007/0158270 A1 | 7/2007 | Geier et al. | 210/656 |
| 2007/0282118 A1 | 12/2007 | Gupta et al. | 554/169 |
| 2009/0025277 A1 | 1/2009 | Takanashi | 44/302 |
| 2009/0069586 A1* | 3/2009 | Oku et al. | 554/170 |
| 2009/0112008 A1 | 4/2009 | McNeff | 554/124 |
| 2009/0156847 A1 | 6/2009 | Banavali et al. | 554/175 |
| 2009/0199460 A1 | 8/2009 | Munson et al. | 44/308 |
| 2009/0255171 A1* | 10/2009 | Dumesic et al. | 44/308 |
| 2010/0077655 A1* | 4/2010 | Bauldreay et al. | 44/437 |
| 2010/0132251 A1 | 6/2010 | Wada et al. | 424/59 |
| 2010/0154295 A1 | 6/2010 | Bazer-Bachi et al. | 44/411 |
| 2010/0313468 A1 | 12/2010 | Jalalpoor et al. | 44/388 |
| 2011/0023353 A1* | 2/2011 | Ciciulla | 44/388 |
| 2011/0047864 A1 | 3/2011 | Bhan et al. | 44/307 |
| 2011/0252697 A1 | 10/2011 | Boensch et al. | 44/388 |

FOREIGN PATENT DOCUMENTS

| | | | | |
|---|---|---|---|---|
| WO | 2006094986 | 9/2006 | ............ | C11C 3/00 |
| WO | 2007025360 | 3/2007 | ............ | C11C 3/10 |
| WO | 2007076163 | 7/2007 | | |
| WO | 2009058324 | 5/2009 | ............ | B01J 31/02 |
| WO | 2009099655 | 8/2009 | ............ | B01D 15/00 |
| WO | 2009132670 | 11/2009 | ............ | C10L 1/02 |
| WO | 2010057660 | 5/2010 | ............ | B01J 20/08 |

OTHER PUBLICATIONS

Wang, Y., et al., Preparation of microspherical magnesia-rich magnesium aluminate spinel catalyst for methanolysis of soybeanoil, 2008, Chemical Engineering Science, vol. 63, pp. 4306-4312.*
ISR & Written Opinion dated Aug. 17, 2012 for PCT Appln No. PCT/US12/38947.
Hawley's Condensed Chemical Dictionary, Eleventh Edition, Sax et al., 1987, "Rare Earth", p. 996.

* cited by examiner

Flow chart of Biodiesel process incorporating a Catalytic purification step – Option 1

Flow chart of Biodiesel process incorporating a Catalytic purification step – Option 2

CATALYTIC PURIFICATION OF FATTY ACID ALKYL ESTERS USED IN FUELS

RELATED APPLICATIONS

This application claims priority and the benefit of the filing date of U.S. Provisional Patent Application No. 61/499,565 filed Jun. 21, 2011 and 61/594,730 filed Feb. 3, 2012, and International Application No. PCT/US2012/038947 filed May 22, 2012, the disclosures of which are hereby incorporated herein by reference.

FIELD OF THE INVENTION

This invention relates to the purification of fatty acid alkyl esters, particularly those esters known as biodiesel, which are prepared from transesterification reactions involving triglycerides derived from animal or vegetable sources and an alcohol.

BACKGROUND

Biodiesel fuel is frequently made from triglycerides derived from animal or plant sources. The triglyceride is reacted with an alcohol, typically, methanol in the presence of a catalyst (typically sodium methoxide) in a transesterification reaction to produce fatty acid alkyl esters (biodiesel) and glycerin (a byproduct). The ester fraction is separated from the glycerin layer (e.g., after catalyst neutralization with an acid like phosphoric acid) and then purified using water washing and distillation to decrease the levels of impurities and pass a specification under ASTM D6751 indicative of the availability of the ester for use in colder temperatures. The processed ester is also known as biodiesel. The cold temperature test commonly used today is the Cold Soak Filtration Test (CSFT) as described by ASTM D7501, which is used to measure the product's "cold flow properties".

The cold flow properties of biodiesel depend on the nature of the fatty acid chains of the feedstock (paraffinic versus ° Jennie), as well as the presence of impurities such as monoglycerides (intermediate product in the transesterification reaction) and sterol glycosides (originating from the feedstock) remaining after the purification steps. Sterol glycosides are compounds present in ppm quantities in natural oils. They are typically present in the acylated form which is soluble in the oil. During the transesterification process, these compounds get converted to the non-acylated form of sterol glycosides which have low solubility in the fatty acid alkyl esters. It has been shown that the presence of saturated monoglycerides and the non-acylated sterol glycosides (both with relatively high melting points >40° C.) can cause significant clouding of the biodiesel and result in clogging of fuel filters, especially under cold weather conditions. This phenomenon has been observed in streams containing 100% biodiesel (also referred to as "B100"), as well as streams comprising blends of biodiesel and petroleum derived diesel (also referenced as "BXX" blends, in which the XX is a number reflecting the percentage of biodiesel in the blend). To overcome these problems, the aforementioned ASTM D7501 tests have been implemented in the United States to qualify fatty acid alkyl esters for biodiesel for cold weather performance.

Current methods for purifying fatty acid alkyl ester streams involve low temperature adsorbent approaches, wherein adsorbents bind or otherwise remove impurities from the desired fatty acid alkyl ester. For example:

(1) WO 2009/099655 discloses a cartridge-based solution to process ester product that meets the CSFT. This process comprises two steps for continuous purification of biodiesel, one of which includes the use of an adsorbent or filter-aid.

(2) US 2010/0313468 describes a process of treating biofuels with an adsorbent comprising two different metal oxides including zeolites, silicas, aluminas or combinations thereof.

(3) US 2007/0151146 describes a process utilizing a silica hydrogel, among other samples, for alleviating the "filter-blocking tendency" of biodiesel.

(4) US 2009/0156847 discloses using resin-based adsorbents for biodiesel purification.

(5) U.S. Pat. No. 7,635,398 describes a magnesium silicate product that can remove biodiesel impurities and help pass the CSI-T.

(6) WO 2009/132670 describes clay adsorbents for processing product to meet the CSFT requirement.

Adsorbent processes, however, require frequent regeneration to remove bound species from binding sites, or removal/replacement of the adsorbent to introduce fresh adsorbent. Regeneration in continuous processes, moreover, require either shutting down the system and flushing it with solvent to regenerate the adsorbents, or requiring at least a second adsorbent column containing fresh adsorbent through which the process stream is run while the other column is being regenerated. Distillation processes require capital investment at a significant cost.

It therefore is desirable to have alternative processes, especially those that can be run with less frequent changeover or regeneration of material used to purify the esters, with a lower capital investment cost relative to distillation, as well as have an approach that can be widely adopted regardless of the specific process used to manufacture the fatty acid alkyl ester.

SUMMARY OF THE INVENTION

The process of this invention removes impurities from fatty acid alkyl ester-containing streams, e.g., biodiesel, by using a catalytic process. Typical fatty acid alkyl ester streams produced from conventional transesterification reactions comprise at least ninety percent by weight fatty acid alkyl ester. Such streams also comprise impurities that adversely affect the properties of the esters at temperatures in colder environments. After treatment using the invention, however, the resulting ester stream exhibits improved performance under cold weather conditions, which is typically required for biodiesel. This performance can be measured by methods such as the ASTM 7501 Cold Soak Filtration Test (CSFT).

Generally, the process of the invention treats a fatty acid alkyl ester-containing stream by:

(a) contacting the stream with a catalyst, with optional addition of an alcohol, under catalytic conditions to convert at least one, preferably, some or all of the impurities in the stream to alkyl ester product and/or byproduct, e.g., that does not affect the properties of the desired ester at relatively colder temperatures compared to those in the presence of the unconverted impurity, and (b) recovering a fatty acid alkyl ester (FAAE) stream having reduced amounts of impurities and having improved cold flow properties, e.g., such that the recovered fatty acid alkyl ester stream meets all the specifications desired for use of the product in diesel fuel, including specifications such as the ASTM D7501 CSFT.

Particularly suitable catalysts comprise an oxide of an element or metal selected from the group of elements or metals in Groups 3, 4, 5, 13 and 14 of the Periodic Chart as defined by IUPAC nomenclature. Mixed oxides of the aforementioned elements are also suitable. Particularly suitable oxides include alumina, silica, titania, zirconia, lanthana, and combinations thereof, and particularly suitable mixed oxides include silica-alumina, lanthana-alumina, titania-alumina, zirconia-alumina, titania-silica, titania-zirconia-alumina, lanthana-zirconia-alumina, and the like. Mixed oxides comprising alkaline earth oxide, e.g., magnesium oxide, and Group 3 metal oxide, e.g., alumina, are also generally suitable, and those containing magnesium aluminate spinel are particularly suitable. Mixed oxide compositions further comprising rare earth oxide and an oxide of a Group 5 metal, e.g., ceria and vanadium oxide, respectively have shown to be particularly useful in the invention.

The impurities removed in this process include those typically found in products from transesterification reactions, in which triglycerides, e.g., those from animal or vegetable sources, are converted to fatty acid esters. These impurities include monoglyceride, sterol glycosides, unreacted triglyceride, diglyceride, and/or glycerin. In the case of the glyceride derivatives such as mono-, di- and tri-glycerides, it is especially advantageous to convert these to the fatty acid methyl ester derivatives. It has been shown that FAAE comprising 0.8% by weight or less monoglycerides, and 10 ppm or less sterol glycosides can be recovered from the process of this invention.

Suitable catalytic conditions for the invention comprise contacting the feed stream with a catalyst at a temperature of at least 100° C. Alcohol is optional in step (a) above since fatty acid alkyl esters from transesterification processes frequently comprise sufficient amounts of unreacted alcohol from the initial transesterification process. If additional alcohol is needed, the alcohol can be one selected from the group consisting of methanol, ethanol, propanol, butanol, and mixtures thereof.

The invention can be utilized at various steps of a transesterification process in which a triglyceride is converted to a fatty acid alkyl ester. One particularly suitable process (Process 1) comprises:
(a) introducing triglyceride-containing feedstock and an alcohol as reactants into a reactor selected from the group consisting of continuous fixed bed reactor, continuous stirred tank reactor, and a batch reactor,
(b) contacting the reactants in the reactor with a catalyst in liquid, granulated or powder form;
(c) subjecting the feedstock and catalyst to conditions sufficient to convert triglycerides to products comprising alkyl ester derivatives of the triglycerides, and glycerin, wherein the alkyl ester derivatives of the triglycerides and impurities (e.g., those comprising monoglycerides, diglycerides, unreacted triglycerides, sterol glycosides and, optionally, (a portion of) unreacted alcohol from (a)), are present in an oil phase, and glycerin and (a majority of) the unreacted alcohol from (a) are present in a water soluble phase;
(d) performing product separation to remove the water soluble phase (e.g., glycerin-containing) from the oil phase;
(e) contacting the oil phase separated from (d), optionally containing any residual alcohol, with a catalyst and, optionally, additional alcohol, under catalytic conditions to convert some or all of the impurities in the feed stream to a product or by product (also referred to herein as the purification reaction step), and
(f) recovering a fatty acid alkyl ester stream having reduced amounts of impurities, and thus with improved cold flow properties.

The process of the invention can be used for purification of fatty acid alkyl ester products prepared using homogeneous or heterogeneous catalysts. The invention is particularly suitable for esters prepared using the former type of catalysts, wherein the catalyst in step (b) above can be a liquid homogeneous alkali catalyst, e.g., comprising sodium methoxide or potassium methoxide. In such a case, step (c) further comprises neutralizing the liquid alkali catalyst and optionally performing a water washing step prior to or after the separation step (d).

A process of the invention can also be used to supplement conventional adsorbent or filtration processes for purifying contaminated ester streams produced in Process 1. For example, Process 1 can be modified after step (d), thereby resulting in an overall process comprising the following steps:
(a) introducing triglyceride-containing feedstock and an alcohol as reactants into a reactor selected from the group consisting of continuous fixed bed reactor, continuous stirred tank reactor, and a batch reactor,
(b) contacting the reactants in the reactor with a catalyst in liquid, granulated or powder form;
(c) subjecting the feedstock and catalyst to conditions sufficient to convert triglycerides to products comprising alkyl ester derivatives of the triglycerides, and glycerin, wherein the alkyl ester derivatives of the triglycerides, and impurities, e.g., those comprising monoglycerides, diglycerides, unreacted triglyceride, sterol glycosides and, optionally, residual unreacted alcohol from (a), are present in an oil phase, and glycerin and most of the any unreacted alcohol from (a) is present in a water soluble phase;
(d) performing product separation to remove glycerin product from the oil phase;
(e) removing residual alcohol from the oil phase recovered in (d),
(f) contacting the oil phase with adsorbent or filter aid,
(g) further contacting the alkyl ester-containing oil phase recovered from (f) and any impurities therein with a catalyst and, optionally alcohol, under catalytic conditions to convert some or all of the impurities in the alkyl ester-containing oil phase to a product or by product, and
(h) recovering a fatty acid alkyl ester stream having reduced amounts of impurities.

The process of this invention can also be used in a multiple stage reactor system. Process 1 can therefore be modified after step (d) to include one or more additional transesterification steps, and therefore the process of the invention can comprise,
(a) introducing triglyceride-containing feedstock and an alcohol as reactants into a reactor selected from the group consisting of continuous fixed bed reactor, continuous stirred tank reactor, and a batch reactor,
(b) contacting the reactants in the reactor with a catalyst in liquid, granulated or powder form;
(c) subjecting the feedstock and catalyst to conditions sufficient to convert triglycerides to products comprising alkyl ester derivatives of the triglycerides, and glycerin, wherein the alkyl ester derivatives of the triglycerides, and impurities, e.g., those comprising monoglycerides, diglycerides, unreacted triglyceride, sterol glycosides and, optionally, residual unreacted alcohol from (a), are present in an oil phase, and glycerin and most of the any unreacted alcohol from (a) is present in a water soluble phase;

(d) performing product separation to remove glycerin product from the oil phase;

(e) subjecting the oil phase to further transesterification in one or more reactors with additional alcohol under conditions sufficient to convert triglycerides, diglycerides and monoglycerides to products comprising alkyl ester derivatives of and optionally glycerin;

(f) recovering the alkyl ester derivatives in an oil phase with one or more separation steps; and (g) contacting the recovered alkyl ester derivatives, and any impurities and unreacted alcohol, with a catalyst and, optionally, additional alcohol, under catalytic conditions to convert the impurities in the recovered alkyl ester-containing stream to a product or by product, and (h) recovering a fatty acid alkyl ester stream having reduced amounts of impurities and having properties that meet specifications desired for use of the alkyl ester in diesel fuel, e.g., the alkyl ester has improved cold flow properties.

The multistage reactor process mentioned above can also employ optional catalyst neutralization and water washing steps after a transesterification process comprising a homogeneous catalyst.

DETAILED DESCRIPTION

Figure 1:
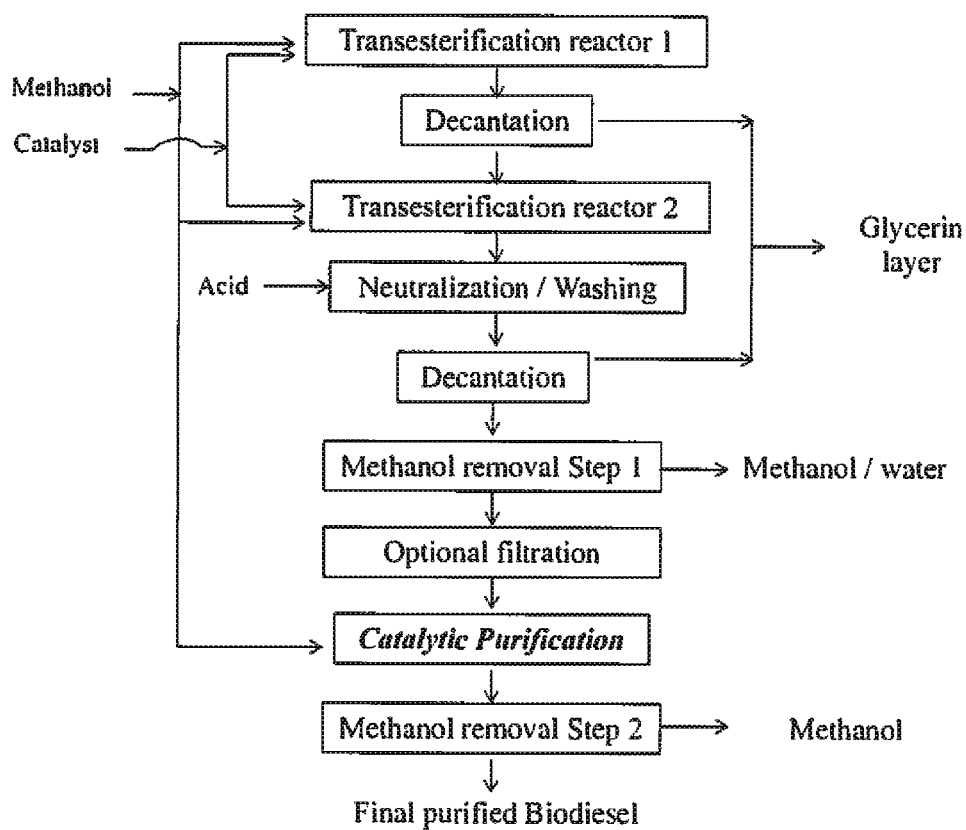
FIG. 1 is a flow diagram illustrating one embodiment of the invention comprising a multistage transesterification reactor system.

As indicated above, the catalytic purification process of this invention can be utilized at various locations within processes for transesterification of glycerides. Exemplary processes and utilization of the invention therein, especially transesterification processes for manufacturing biodiesel, are described in greater detail below.

Triglyceride Feedstocks and Transesterification Reactions

Biodiesel is typically derived from vegetable or animal origin. The feedstock used to make biodiesel can therefore be unrefined vegetable oils free of their phospholipids or gums, recovered oils such as those used for frying, and animal fats with an acid number (AN) in the range 0.5 to 20. Particularly suitable examples of vegetable oils include African oil, palm nut oil and coconut oil, as well as other types of oils such as soya, rapeseed, sunflower, corn, peanut, cotton, shea, crambe, safflower, castor, jatropha, etc. Other less expensive feedstocks that can be used include those of animal fat origin such as beef tallow, poultry fat, fish oil, and trap grease as well as used cooking oils, which are more attractive from a process economics standpoint to a biodiesel producer. These feedstocks primarily are comprised of triglycerides, which comprise of three fatty acid chains linked by a glycerol backbone. Other feedstocks that can be used in this process include algal oil and the like.

The feeds used in transesterification reactions for making biodiesel contain, or are processed to contain, mostly triglycerides. The triglyceride feed may also contain free fatty acid, typically comprising up to 1% by weight free fatty acid. The triglyceride feedstock is then contacted with alcohol in the presence of transesterification catalyst and conditions to produce a fatty acid alkyl ester. The alcohol added to the reactor can be one or a mixture of two or more alcohols conventionally used to convert triglyceride-containing feedstocks to esters. Suitable alcohols include those having one to six carbons, and typically are monoalcohols. Methanol is frequently suitable, but the alcohol can include higher monoalcohols such as ethanol, 1-propanol, isopropanol, 1-butanol, isobutanol, 1-pentanol or 1-hexanol.

The molar ratio of alcohol to triglyceride in a transesterification reaction is generally in the range of 3:1 to 30:1, and typically in the molar ratio of from 5:1 to 25:1. A molar ratio of alcohol to triglycerides less than 3:1 is more likely to lead to less than stoichiometric conversion of triglyceride to fatty acid alkyl esters. Higher molar ratios of alcohol to triglycerides greater than 30:1 are disadvantageous because the presence of increasing amounts of methanol leads to a much higher cost for separation/recycling of the methanol in the downstream processing steps. The selected molar ratio of alcohol to triglycerides in the above range thus represents an economically sensible ratio, outside of which the conversion can no longer be expected when using other conditions described herein, or when using other conditions conventionally used in reactions of the type described herein.

The catalyst used in the transesterification reaction can be a homogeneous or heterogeneous catalyst. Suitable homogeneous catalysts include alkali methoxide, alkali hydroxides and mixtures thereof, including but not limited to, sodium methoxide, potassium methoxide, sodium hydroxide, and potassium hydroxide. Suitable heterogeneous catalysts include those described in US Patents WO 2006/050925; US 2009/0069586; U.S. Pat. No. 5,908,946; WO 2007/025360; or U.S. Pat. No. 7,420,073, the contents of which are incorporated herein by reference.

The ester derivative produced depends on the number of carbons in the alcohol. Frequently, methanol is used in the transesterification reaction and reactions using methanol produce fatty acid methyl esters, also known as FAME. Ethyl, propyl, butyl, pentyl, and hexyl esters are produced, respectively, when ethanol, propanol, butanol, pentanol, and hexanol are used in the transesterification reaction.

The transesterification reaction is carried out in the presence of the catalyst under conventional conditions. The reaction can be carried out in batch reactors, in a continuous (e.g. stirred) tank reactor, as well as in fixed-bed reactors. The reactor conditions should be those sufficient to convert the triglycerides to esters using transesterification. The conditions (also referred to as transesterification conditions) include a temperature in the range of 40° C. to 250° C., more typically in the range of 60 to 200° C. Typical pressures would be in the range of 1 to 100 atmospheres (atm), more typically 1 to 50 atm, with the final pressure dependent on the specific alcohol and the reaction temperature used in the reaction. Lower pressures can lead to a loss of alcohol from the reaction mixture, thereby reducing ester yield, whereas higher pressures are energy-intensive and are thus, in certain circumstances, economically disadvantageous. It is therefore desirous to select pressures approximately corresponding to the vapor pressure of the selected alcohol at the temperature selected.

A particularly suitable reactor is a batch reactor or continuously stirred tank reactor to provide maximum economic benefit to the biodiesel producer. See WO 2009/058324 illustrating such reactors.

A fixed bed reactor operation is also useful, and can be performed in any type of flow configuration of the reactants, up flow, down flow or trickle bed mode. The up flow mode is particularly preferred to ensure optimum catalytic performance for the transesterification reaction.

For batch reactors, the residence time for the reactant triglyceride and alcohol is usually between 5 and 100 minutes, more typically between 20 and 60 minutes. For continuous reactors, the liquid hourly space velocities range from 0.01 to 5 $h^{-1}$, more typically 0.1 to 0.5 $h^{-1}$.

As discussed later below, using the invention in a multiple stage transesterification reactor system provides an efficient and economically desirable process for making alkyl ester derivatives suitable for fuels. It is envisioned that the invention is particularly suitable for these systems.

Impurities in Fatty Acid Alkyl Ester Products

Once the triglycerides and alcohol react in the transesterification reactor, the effluent is further processed to recover fatty acid alkyl ester product. The product esters are present primarily in a phase that is not water soluble (also referred to herein as the "oil phase"), and any glycerol (also known as glycerin) produced and most of the unreacted methanol are primarily in the water soluble phase. The separation process comprises separating the glycerol phase and oil phase comprising the ester and subsequently removing the remaining alcohol through a flash drying or stripping step. The removal of the water soluble glycerol-rich phase by means of phase separation is preferably carried out at temperatures between 60° C. and 150° C. The phase separation is likewise preferably carried out at a pressure corresponding to the vapor pressure of the alcohol. The pressure is preferably somewhat higher than the vapor pressure of the alcohol used in the process. This separation can be conducted by distillation or decantation. The separation process can be conducted in a batch or continuous manner.

In the case of homogeneous transesterification processes involving alkali-based catalysts, typically a catalyst neutralization step (involving the addition of an acid such as phosphoric acid or sulphuric acid) is performed along with one or more water washing/separation steps prior to the removal of methanol discussed above.

Impurities and/or contaminants, however, are not completely removed during the aforementioned separation processes, and up to 10% by weight impurities can still be present in the desired ester product. For example, impurities may include, but are not limited to, soap, colors, odors, unreacted catalyst, metals and metallic compounds, phosphorus, monoglycerides, diglycerides, triglycerides, sterol glycosides, nitrogen compounds, sulfur compounds, acidic compounds, free and total glycerin, methanol, chlorophyll, water, and sediment. These impurities are known to detract from or detrimentally affect performance of the ester as a fuel. Of these, the residual monoglycerides, diglycerides and triglycerides result from incomplete conversion during the transesterification process. Sterol glycosides are present in ppm level quantities in the vegetable oils. They are soluble in oils when in the acylated and non-acylated form. During transesterification processes that use conventional alkali-based catalysts, sterol glycosides are converted to a non-acylated form. The non-acylated forms of sterol glycosides, however, unlike in the vegetable oil, have low solubility in the ester product, and it is suspected that these forms of glycosides, along with saturated monoglycerides, cause problems with cold weather performance for biodiesel such as clogging of fuel filters etc.

Biodiesel manufacturers therefore have heretofore treated the ester product with adsorbents, filters or membranes to remove the impurities. Such treatments are sometimes referred to as "polishing" treatments. Adsorbents suitable for these treatments are well known in the art. Suitable polishing adsorbents include, but are not limited to, silica gel, resins, magnesium silicate, bleaching earth and diatomaceous earth. The polishing treatment can be performed in a batch or a continuous mode of operation and could be performed at temperatures ranging from 1° C. to 100° C. This invention, however, can be used as a supplement to, or in place of adsorbent, filter or membrane based processes.

Catalytic Purification

The process of this invention comprises a catalytic purification process wherein the impurities are converted chemically to other compounds at conditions that are not preferred for adsorption processes such as elevated temperatures (>100° C.) and pressures. These processes are considered catalytic because in the absence of a catalyst, the conditions used in the process alone do not convert the impurities. This difference is also evidenced by the desired product yields or purity shown after a period of time during which an adsorbent's capacity would have been exhausted. It is believed that the catalyst and associated conditions in the process catalytically convert the saturated monoglycerides to fatty acid alkyl esters, and the non-acylated sterol glycosides are converted to byproducts comprising fractions of the original molecule with the overall fatty acid alkyl ester product exhibiting superior cold flow properties. It is therefore believed that the byproducts do not adversely the affect the cold flow properties of the ester compared to esters comprising the unconverted monoglycerides and sterol glycosides. As described earlier, fatty acid esters comprising 0.8% by weight or less monoglycerides and 10 ppm or less sterol glycosides can be recovered from the invention. The fatty acid alkyl ester recovered from the invention more suitably comprises 0.5% by weight or less monoglycerides, but with amounts of 0.4% or less being preferred, and amounts of 0.2% by weight or less, monoglycerides being even more preferable. Fatty acid alkyl esters comprising 5 ppm or less, or even 2 ppm or less, sterol glycosides are particularly suitable.

The catalyst can be in a granulated form (granules, beads, spheres, tablets, and extrudates), for example, those appropriate for use in a fixed bed reactor designed for continuous operation. The granulated forms can have dimensions in the range of 0.1 to 10 mm, and more typically, in the range of 0.5 to 5 mm. The form can be of any shape, for example, cylindrical, trilobe or quadrilobe. The granulation process can be a combination of mixing and extrusion. The formulation for the extruder feed may optionally comprise additional oxide for improving the mechanical strength of the granulated material (measured as crush strength), extrusion aid such as methyl cellulose (for example, commercially available as Methocel), and optionally acids such as nitric acid for peptization and for enhancing mechanical strength to the granulated material. In addition, the water level is adjusted to optimize the extrudability of the catalyst. The formulation forming the extruder feed is first mixed in a Sigma or an Eirich mixer and is then extruded through a commercially available single screw or twin screw extruder. The extruded material is then dried and calcined to form the finished catalyst. Granulated particle embodiments are typically calcined during the forming process at temperatures from 300° C. to 1200° C., more preferably from 400° C. to 1000° C. and most preferably from 500° C. to 900° C. The catalyst can also be granulated into a spherical form with similar ingredients mentioned above, but done so in a Eirich or a Nauta Mixer, followed by similar drying/calcination processes. The catalyst could optionally be regenerated for reuse but the preferred mode is once-through.

Catalyst in powder form can be utilized in batch or continuous stirred tank reactors. The powdered forms generally comprise spray dried particles, and have a nominal particle size in the range of 1 to 1000 microns, frequently in the range of 10 to 500 microns, and more typically in the range of 30 to 200 microns. In this case, a filtration step is typically employed to separate the purified biodiesel product from the catalyst powder.

The oxides or mixed oxides described above and used to make the catalyst of this invention can be characterized as either acidic or basic. For example, acidic oxides include combinations of alumina and silica, and exemplary basic oxides include lanthana and cerin. Titania, zirconia, alumina and vanadia are considered amphoteric, and therefore capable of acid or base character depending on the environment in which they are used. A single metal oxide site at any given instant is either a Bronsted acid if terminated by —OH, i.e. the oxygen is protonated, a Lewis acid if the metal is coordinatively unsaturated, i.e. lacking full oxygen coordination such as an Al within a silica matrix, or a base (which can function in either the Lewis or Bronsted sense) if terminated by an M-O⁻, i.e. the oxygen is unprotonated.

The oxides or mixed oxides, either amorphous or crystalline, can be prepared using conventional preparation methods and techniques. Single or mixed oxides can be prepared via precipitation or co-precipitation using salts of the selected element, but can also be prepared via gelation, forming solid solutions, or impregnation. For example, one preferred embodiment comprises impregnating one element onto a carrier made from another suitable element, either in oxide form, or oxide precursor form.

Suitable oxides and mixed oxides include those commercially available in powder, which can be further processed into shaped forms. For example, Catapal™ aluminas from Sasol and TIONA® titanium dioxides from Cristal Global can be used to make the invention. Suitable oxides are also available in pre-formed shapes.

In some embodiments, such as a formed catalyst or other compositions comprising oxide precursors, it may be necessary to further process the composition. For example, oxide precursors generally require further processing to form oxides, or crystalline oxide compounds. Calcining under appropriate conditions is one method to do so. Further processing of mixed oxides may also be necessary to form spinel structures, if desired, e.g., magnesium aluminate spinel can be formed by calcining mixed magnesia/alumina under appropriate conditions. Methods for making the oxides, oxide precursors and formed shapes thereof are known and illustrated in Farrauto and Bartholomew, Fundamentals of Industrial Catalytic Processes, Blackie Academic & Professional, pp. 88-99 (1997), the contents which are incorporated by reference. See also, further description below, and Krylov, O. V. 1970 Catalysis by Nonmetals; Moss, R. L., 1976. Preparation and Characterization of Supported Metal Catalyst, in Experimental Methods in Catalytic Research, v. II, Ch 2, pp. 43-94; Stiles, A. B., Catalyst Manufacture: Lab, and Commercial Preparations Surface area, dispersion of oxides within the catalyst comprising mixed oxides, presence and nature of crystalline phases, if any, and specific of combination of oxides, can affect the catalytic activity of the catalyst composition chosen. Therefore one can tailor the composition and/or its properties to have the desired activity for a particular application.

As mentioned above, suitable mixed oxide catalysts include oxides of alkaline earth metals (including but not limited to Mg, Ca and combinations thereof) and Group 13 metals, such as aluminum. Particularly suitable embodiments of the invention, for example, comprise 20 to 60% by weight magnesium oxide, and 30 to 70% by weight alumina. Embodiments of the catalyst comprising 30 to 45% by weight magnesium oxide, and 45 to 60% by weight alumina are also suitable. The mixed metal oxide, alkaline earth metal embodiments of the catalyst of this invention may further comprise an alkaline earth metal aluminate spinel, as discussed earlier. The term spinel in the context of this invention refers to the conventional definition of a spinel phase, i.e., a crystal structure possessing double oxides having a formula of $AB_2O_4$, wherein A and B represent a metal element. The composition of the spinel used in this invention can therefore vary depending on the metals selected. For example, a spinel formed from an alkaline earth and Group 13 metal such as aluminum is an aluminate spinel. Therefore metal B is trivalent Al, and metal A is an alkaline earth metal, e.g., magnesium, thereby making such a spinel an alkaline earth metal aluminate spinel. Spinel structures are crystalline, and possess an octahedral profile that belongs to a closely packed, oxygen-containing cubic lattice of $AB_2O_4$, as the lattice unit. Processes for making spinels are known and described in U.S. Pat. Nos. 4,492,678 and 4,728,635, the contents of which are incorporated by reference. Briefly, a mixture of the two selected metals are formed, a mixed oxide is precipitated, and the precipitate heated, e.g., via calcination, to form a mixed oxide having the aforementioned crystal structure.

Generally, when using spinel-containing embodiments, the catalyst can comprise spinel in amounts ranging from 5 to 95% by weight of the catalyst composition, more preferably 35 to 80 wt % and most preferably 55 to 75 wt %. The spinel content of the composition can be measured using x-ray diffraction. The position of the peak in the XRD pattern for the spinel of this invention depends on the temperature of formation of the spinel when calcined.

The spinel used in this invention preferably has a formation temperature, i.e., calcination, temperature, in the range of 500 to 700° C. This is different from the formation temperatures of spinels derived from other materials such as hydrotalcites. Hydrotalcite compositions typically form magnesium oxide, as well as alumina, at temperatures less than 500° C., and have to be calcined at temperatures as high as 800 to 900° C. before spinel forms as mentioned in US 2010-0298586.

Depending on the mixed oxides selected, or added, there also may be other types of spinel present in the catalyst composition, including zinc aluminate-, calcium aluminate-, or lanthanum aluminate-containing spinels, such as those described in US 2010-0298586. Most catalyst embodiments of this invention however do not contain more than 20% by weight of the additional mixed oxide or additional spinel, and more typically, no more than 10% by weight.

The catalyst of this invention can comprise certain metal oxides, such as alumina, that provide binding properties to a formed catalyst, in addition to providing catalytic properties to the resulting catalyst. The catalysts of this invention, however, can also comprise one or more additional oxides that are not substantially catalytically active, but do provide binding properties or promote structural stability to the finished product. For example, a mixed magnesium oxide/ alumina catalyst can comprise other mixed oxides or silicates that include, but are not limited to, calcium/alumina mixed oxide or calcium silicate or magnesium silicate including ones those derived from natural sources or synthetic processes such as those from the cement industry, and mixed oxides from fillers, such as clay and other silica/aluminas. The catalyst can contain oxides (such as $SiO_2$ or $ZrO_2$) that are added for improving thermal stability. These oxides can be added in powdered form to the mixed oxide powder added for catalytic properties, or as powders to the mixer during a granulation process using conventional methods.

The catalyst used in the invention may optionally further comprise rare earth oxide, as mentioned above. The rare earth oxide in the catalyst of this invention can be an oxide(s) of one or more of the elements of the Periodic Table having atomic numbers from 57 to 71. The metals within this range of atomic numbers include lanthanum (atomic number 57) and lanthanide metals. See, *Hawley's Condensed Chemical Dictionary*, 11$^{th}$ Edition, (1987). Suitable rare earth oxides therefore include oxides of cerium, lanthanum, neodymium, erbium, dysprosium, holmium, thulium, lutetium, and ytterbium. The rare earth oxide can be added to a mixed metal oxide in accordance with processes described in the aforementioned U.S. Pat. No. 4,728,635. The rare earth oxide may also contain yttrium oxide, which is frequently present in mined rare earth. Processes for adding the rare earth oxide, include, but are not limited to, associating the rare earth metal in the metal oxide precursors when making the mixed oxide, or impregnating rare earth onto a base of mixed oxide and alkaline earth metal aluminate spinel containing composition. The rare earth oxide may be present in the catalysts at an amount of 1 to 30% by weight. Rare earth oxide would more typically be in the range of 5 to 20% by weight and more preferably in the range of 10 to 15% by weight. The weight measurements of rare earth oxide refer to that reported as an oxide in elemental analysis techniques conventionally used in the art, including but not limited to, inductively coupled plasma (ICP) analytical methods.

The catalyst may optionally further comprise oxide of a Group 5 metal such as vanadium or niobium. The Group 5 metal oxide can be present in amounts of 0.001 to 10% by weight, more typically in the range of 1 to 5% by weight, and can be added to the catalyst composition in a manner similar to that used to add the rare earth oxide component. See for example, U.S. Pat. No. 4,728,635. Unless expressed otherwise herein, weight measurements of the oxide of Group 5 metal or Group 5 compounds refer to that reported as an oxide in elemental analysis techniques conventionally used in the art, including but not limited to, Inductively Coupled Plasma (ICP) analytical methods.

The Group 5 metal and rare earth are particularly suitable for inclusion in spinel containing embodiments of the invention that are prepared from magnesia alumina mixed oxides.

The catalytic purification process of the invention can be carried out in a reactor similar to that described earlier with respect to transesterification reactions converting the triglyceride-containing feedstock. A fixed bed continuous reactor is particularly suitable. Suitable catalytic conditions comprise temperatures, residence times, and pressures suitable for converting the aforementioned impurities into molecules and byproducts that will not detrimentally affect the resulting ester as fuel, or its properties that affect its properties during storage or use. The reactor conditions can vary and depend on the concentration of impurities, the type of impurities, and the desired purity. The conditions can range from 40° C. to 250° C. Particularly suitable conditions include a temperature of at least 100° C., and more particularly in the range of 100° C. to 200° C., pressures in the range of 1 to 15 atm, and liquid hourly space velocity (LHSV) of 0.01 to 5.0 h$^{-1}$ are suitable for continuous processes, with a LHSV in the range of 0.05 to 2 h$^{-1}$ being particularly suitable.

Certain reactors require a filtration step after the purification reaction step to separate the catalyst from the purified fatty acid alkyl ester product. This is especially preferred when the purification reaction step is carried out in a batch or continuously stirred tank reactor wherein the catalyst used is in powder form.

The catalytic process of this invention can be carried out at process stages in which conventional adsorbent processes are carried out to purify fatty acid alkyl ester streams destined for use in biodiesel. The invention has been shown to be particularly useful in purifying streams comprising at least 90% by weight fatty acid alkyl ester, more likely streams comprising at least 95% by weight fatty acid alkyl ester and is very useful for purifying streams comprising at least 97% by weight fatty acid alkyl esters. The impurities in these streams can be the remaining fraction in the stream.

This process can therefore be incorporated at any point after the transesterification reaction step in the biodiesel manufacturing process, but most preferably incorporated after catalyst neutralization/washing with respect to processes using homogeneous catalyst. In this process, the biodiesel is washed with warm, slightly acidic water to neutralize the ester product containing residual alkaline homogeneous catalyst and remove them as salts. One or more additional washing steps employing water may also be employed in combination with the neutralization step. Typically a decantation step is employed after these steps to perform separation of the glycerin layer containing glycerin, methanol and salts.

Indeed, the invention is particularly useful in transesterification processes using alkali catalysts. Many transesterification processes utilize liquid alkali catalysts, e.g., sodium methoxide, which, as mentioned earlier, result in non-acylated sterol glycosides that are not as soluble in fatty acid alkyl esters, especially at lower temperatures. Processes using other types of alkali or alkaline earth catalysts, e.g., heterogeneous catalysts such as those based on calcium or lanthanum, may also benefit from this invention.

Alternatively, the process can be used either before or after methanol recovery typically carried out by distillation or stripping. For example, the invention can be used prior to methanol recovery, because the presence of residual methanol can promote the conversion of residual monoglycerides in the impurities by transesterification to form fatty acid alkyl esters.

Use of the Invention with Multiple Stage Reactors

The invention is particularly adaptable for use at one or more of several points in a multistage reaction process system.

For example, the invention can be utilized as a process step in a two-stage fixed bed continuous or a two stage batch catalytic process, as shown in FIG. 1. In the first stage of the process, triglyceride in a refined oil or fat feedstock is converted to a product, e.g., containing about 70-90 wt % alkyl esters (typically methyl esters) with the remaining composition comprising unreacted triglycerides (TG), residual monoglycerides (MG) and diglycerides (DG) and small quantities of other impurities such as ppm levels of sterol glycosides. Suitable conditions for this first reaction include a temperature in the range of 40° C. to 250° C., more typically in the range of 60 to 200° C., pressure in the range of 1 to 100 bar, more typically 1 to 50 bar, and alcohol to feedstock molar ratio in the range of 3:1 to 30:1 (more typically 5:1 to 25:1). In the case of a fixed bed continuous process, the LHSV is in the range of 0.05 to 5 h$^{-1}$ (more typically 0.1-0.5 h$^{-1}$). In the case of a batch process, the residence time for the reactant triglyceride and alcohol can be between 5 and 100 minutes, more typically between 20 and 60 minutes. This process stream is sent to a decanter to separate the glycerin/methanol layer from the oil layer. The intermediate step of removing glycerin potentially helps to avoid equilibrium limitations for transesterification facilitating the complete conversion of TG to FAME. A typical composition of oil product after the separation of glycerin/methanol comprises 80% alkyl ester or more by weight (e.g., 83%), and less than 10% each by weight of TO (e.g., 6%), MG (e.g., 6%), and DG (5%). The oil is subsequently sent to a second reactor which converts TG/MG/DG into alkyl ester, e.g., FAME, with additional alcohol, e.g., methanol. The conditions in the second reactor are typically similar to that in the first reactor. The product of the second reactor is then processed through a decanter, wherein the resulting stream is typically, essentially all alkyl ester (e.g., greater than 95 wt. %). The process of this invention can therefore be used to treat product from the second reactor.

Figure 2:
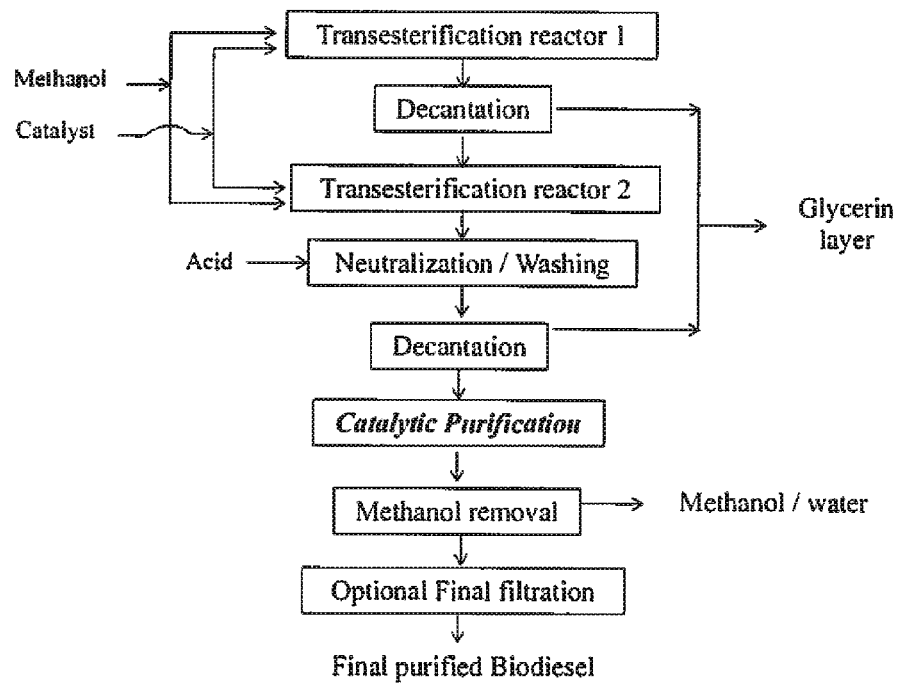
FIG. 2 is a flow diagram illustrating another embodiment of the invention, also comprising a multistage transesterification reactor system.

FIGS. 1 and 2 illustrate specific embodiments of the invention as utilized in exemplary multistage reactor-based transesterification processes, and more specifically, in connection with other process steps taken when processing the ester, e.g., product separation processes such as decantation, washing steps and alcohol removal steps. Moreover, whereas FIG. 1 illustrates a process in which unreacted alcohol from the transesterification reactors is removed from the ester product prior to catalytic purification, FIG. 2 illustrates a process in which alcohol is not removed until after the invention is carried out, and thereby the process of the invention can use residual unreacted alcohol from the transesterification reactors.

The invention is also suitable for further purifying fatty acid alkyl ester that had previously been treated with conventional adsorbents. Conventional adsorbent processes are known. For example, conventional processes comprise treating the ester with silica hydrogel, resinous adsorbents, magnesium silicate, and/or clay. See WO 2009/099655; US 2007/0151146; US 2009/0156847; U.S. Pat. No. 7,635,398; and WO 2009/132670; the contents of which are incorporated by reference.

As discussed above, a goal of the invention is to produce a stream comprising fatty acid alkyl esters that has improved cold flow properties, preferably such that the esters meet the cold flow property specification requirement such as that mandated by the ASTM D7501 CSFT. The catalytic process converts some or all of the impurities in the initial stream to products or by products which do not significantly detract from the ester as a fuel, e.g., combustible material suitable powering an internal combustible engine. Accordingly, esters treated with the invention have shown to meet specifications listed below.

| Biodiesel Standards | | EUROPE | USA |
|---|---|---|---|
| Specification Applies to | | EN 14214 FAME | ASTM D 6751 FAAE |
| CFPP | ° C. | *country specific | |
| Cloud point | ° C. | | *report |
| Methanol | Wt. % | 0.20 max | 0.2 max or Fp <130° C. |
| Monoglyceride | Wt. % | 0.8 max | — |
| Diglyceride | Wt. % | 0.2 max | — |
| Triglyceride | Wt. % | 0.2 max | — |
| Free glycerol | Wt. % | 0.02 max | 0.02 max |
| Total glycerol | Wt. % | 0.25 max | 0.24 max |
| CSFT | sec | | 360/200 |

In some instances, the invention at least improves the cold flow properties, e.g., such that the total time to pass through a filter prescribed in the CSFT is 200 seconds or less, which is considered to be the winter specification of the CSFT.

To further illustrate the present invention and the advantages thereof, the following specific examples are given. The examples are given as specific illustrations of the claimed invention. It should be understood, however, that the invention is not limited to the specific details set forth in the examples.

All parts and percentages in the examples as well as the remainder of the specification that refers to solid compositions or concentrations are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Preparation of Catalyst A

Catalyst A was prepared as follows. To a mixture of water and alumina (Catapal-C from Sasol) in a Cowles mixer, formic acid was added to make a peptization slurry. Subsequently MgO was added to the alumina slurry followed by cerium nitrate and the slurry was milled with a media loading of 80% and a mill feed rate of 0.9 gallons/min. The mixed slurry was pumped to a Bowen spray dryer with a wheel atomizer and a speed of 13500 rpm, targeting an inlet air temperature of 345° C. and an outlet air temperature of 150° C. The catalyst was subsequently calcined in a rotary calciner at 595° C. The slurry was dried as per the above-mentioned procedure and the resulting catalyst had the composition of 53% Al$_2$O$_3$/37% MgO/10% CeO$_2$ by weight.

Preparation of Catalyst B

Catalyst B was prepared using a similar procedure as that for Catalyst A except that a measured amount of vanadium oxalate was added to the slurry mixture before the spray drying step. The resulting mixed oxide had the composition of 52% Al$_2$O$_3$/36% MgO/10% CeO$_2$/2% V$_2$O$_5$ by weight.

Figure 3:
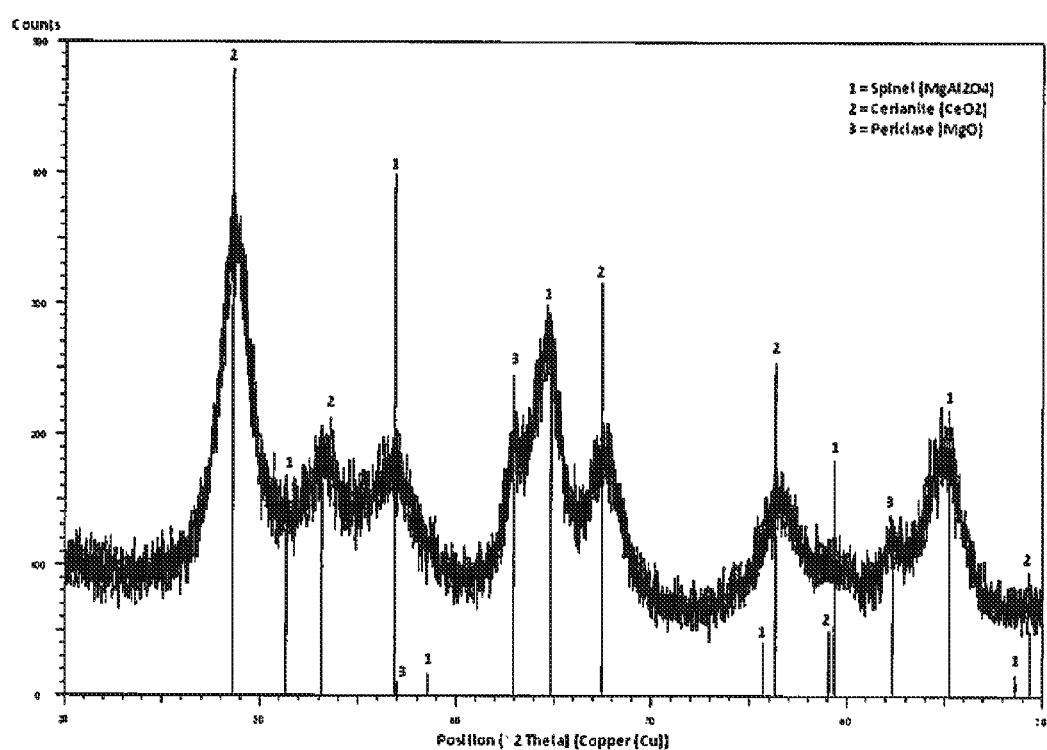
FIG. 3 is an X-ray diffraction pattern of Catalyst B described in the Examples.

The X-ray diffraction scan of this catalyst shown in FIG. 3 confirms the presence of the $MgAl_2O_4$ spinel phase.

Test 1

Evaluation of the Catalytic Concept in a Batch Reactor

The batch reactor experiments were conducted as follows. The impure biodiesel sample used for the tests was a palm-based biodiesel containing negligible levels of methanol but appreciable levels of the impurities, monoglycerides (0.66 by weight) and sterol glycosides (69 ppm). 330 ml of this biodiesel sample was added to a beaker and heated up in an oil bath to 140° C. The powder catalyst (Catalyst A) was dried for 1.5 h at 200° C. and then added to the biodiesel at 3% by weight. The test was carried out at 140° C. at ambient pressure for 60 min with the final 15 min being under vacuum. At the completion of the reaction, the catalyst was separated from the biodiesel using a glass fiber filter either at 140° C. or at 21° C. The purified biodiesel was then tested for its cold flow properties using the standard ASTM D7501 CSFT methodology.

Figure 4:
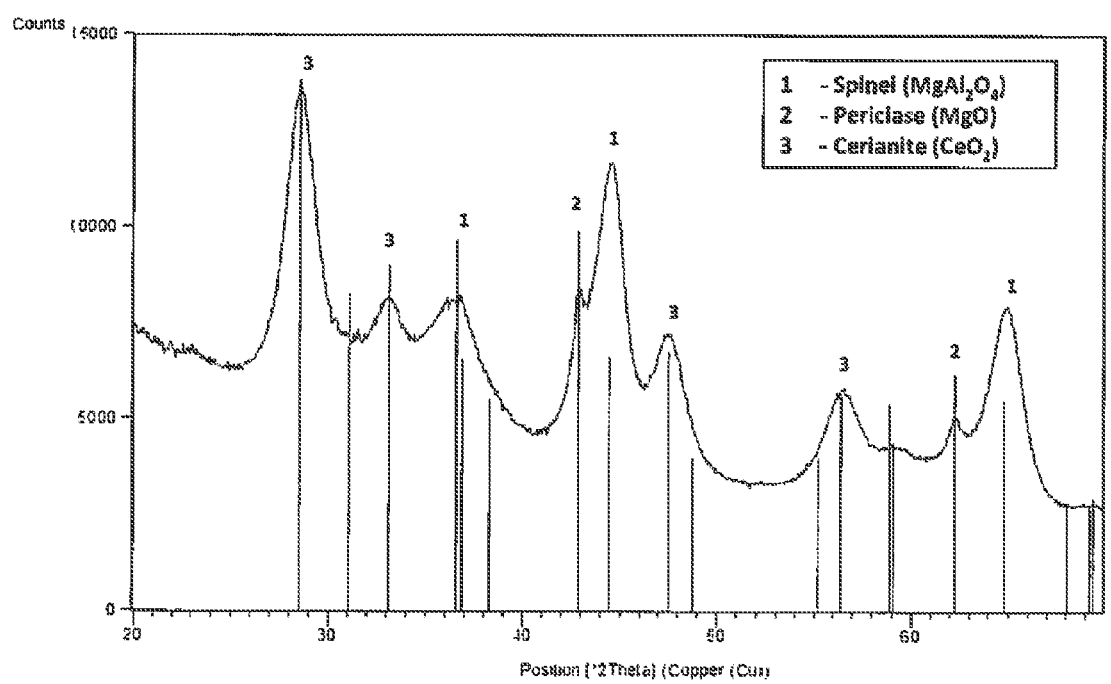
FIG. 4 is an X-ray diffraction pattern of Catalyst D described in the Examples.

Table 1 summarizes the results from the batch tests. Biodiesel that is heated up to 140° C. without any catalytic treatment and filtration does not pass the CSFT. These tests show that the treatment with Catalyst A enables the biodiesel to pass the CSFT with reasonable filtration times (<10 min). It is also shown that the observed effects are independent of the size of the used filters (0.7 μm vs. 5-12 μm). In addition, analytical results indicate that the significant improvement in cold flow properties is indeed due to the reduction in the amount of monoglycerides and sterol glycosides in the biodiesel.

catalyst was designated as Catalyst C. The X-ray diffraction pattern for this catalyst also confirms the presence of the $MgAl_2O_4$ spinel phase (FIG. 4).

Test 2

Evaluation of the Catalytic Purification Concept in a Fixed Bed Reactor for Process 1

The fixed bed reactor test was performed in up-flow mode with 13 cc of Catalyst C extrudates that had been crushed and sieved through 10 mesh and above 20 mesh. The experiment was carried out at a temperature of 180*C, a pressure of 4 psi and LHSV of 0.5 $h^{-1}$. The biodiesel sample used for the experiments was a final filtered soy oil-based biodiesel containing 0.52% by weight monoglycerides (to simulate Process 1—After the methanol removal and optional filtration steps—with methanol addition to the biodiesel containing very little water (See FIG. 1). To simulate Process 1 the final filtered biodiesel sample was spiked only with methanol to the 1% weight level. The liquid flow after the reactor was sent through a back-pressure regulator to a fraction collector that was programmed to collect 8 mL of sample at predetermined time intervals with the total duration of the run being 150 h. Each sample analyzed by GC according to the ASTM D6584 method with an Agilent 5890 Gas Chromatograph equipped with a MXT Biodiesel TG and Integra Gap columns (14 m×0.53 mm dia, 0.16 micron thickness) using a Flame Ionization Detector. Prior to GC injection, each sample was mixed with an internal standard (Tricaprin), and then derivatized using a silylating agent MSTFA (1:1 volume ratio) diluted with n-heptane. The results from this test are summarized in Table 2. It is observed that significant reduction in monoglycerides

TABLE 1

Catalytic Purification in Batch Mode

| | Filtration Conditions | | | Cold Soak Parameters | | | Chemical Analysis | | | | |
|---|---|---|---|---|---|---|---|---|---|---|---|
| Material used | Filtration Temp [° C.] | Filter Size | Filtration Time (min) | Temp. [° C.] | Time [sec] | Filtered Amount [ml] | Glycerin wt % | Monoglycerides wt % | Diglycerides wt % | Triglycerides wt % | Sterol glycosides ppm |
| None | 140 | 5-12 μm | 0.5 | 24.8 | 720 | 300 | 0.01 | 0.66 | 0.15 | 0.21 | 69 |
| 3.0 wt % Catalyst A | 140 | 0.7 μm | 1.3 | 25.3 | 144 | 300 | <0.001 | 0.44 | 0.16 | 0.23 | 4 |
| 3.0 wt % Catalyst A | 21 | 5-12 μm | 74 | 25.5 | 162 | 300 | <0.001 | 0.44 | 0.16 | 0.23 | 4 |

Preparation of Catalyst C

The powder precursor to Catalyst C was prepared using the same procedure as that for Catalyst B except that no calcination step was performed after spray drying. The resulting spray dried product was mixed with water and an extrusion aid (methyl cellulose) and mixed in a 2-gal Eirich mixer for 9 minutes at low speed. The water addition was adjusted to ensure that the resulting granulated material was consistent enough to be extruded. Extrusion was performed using a 4" Bonnet single screw extruder with a screw rotational speed of 20 rpm through a die fitted with cylindrical buttons in order to achieve a 1/32" average diameter. The extrudates were dried overnight at 120° C. in a convection oven and finally calcined in a batch rotary calciner at 650° C. for 1 h with an air flow of 8 L/min. The resulting without a substantial increase in the diglyceride content (undesirable effect) can be achieved with this catalytic process concept.

TABLE 2

Catalytic Purification in a Fixed Bed Reactor

| Time on Stream (h) | Monoglycerides (wt %) | Diglycerides (wt %) |
|---|---|---|
| Inlet | 0.522 | 0.150 |
| 24 | 0.085 | 0.230 |
| 51 | 0.258 | 0.226 |
| 102 | 0.294 | 0.224 |
| 150 | 0.322 | 0.218 |

Test 3

Fixed Bed Reactor Test with Glass Beads

To rule out the presence of any thermal conversion, a test was performed with glass beads. The fixed bed reactor mentioned above was packed with 12 cc of glass beads. The test was performed with the same procedure as that used for Test 2 except that the conditions used were: a reactor temperature of 180° C., pressure of 60 psi and LHSV of 1.0 $h^{-1}$. Negligible conversion of monoglycerides was observed confirming the lack of non-catalytic conversion.

Preparation of Catalyst D

A pre-weighed amount of Catapal-C alumina received from Sasol was added to a 2-gal Eirich mixer along with pre-weighed amounts of a mixture of nitric acid (70% concentration) and water. The ingredients were mixed for 8 min at the low speed setting. The water addition was adjusted to ensure that the resulting granulated material was of adequate consistency to be extruded. Extrusion was performed using a 4" Bonnet single screw extruder with a screw rotational speed of 20 rpm through a die fitted with quadrulobe buttons in order to achieve a 0.05" average diameter. The extrudates were dried overnight at 120° C. in a convection oven and finally calcined in a rotary calciner (6" internal diameter, four zones, 4 rpm rotational speed) at 649° C. with a feed rate of 129 g/min with an air flow of 3-4 L/min. The resulting catalyst was designated as Catalyst D and had a surface area of 210 $m^2/g$ and a $N_2$ pore volume of 0.60 cc/g.

Preparation of Catalyst E

A pre-weighed amount of Siral 30 alumina received from Sasol (containing 30 wt % $SiO_2$) was added to a 2-gal Eirich mixer along with preweighed amounts of methyl cellulose (extrusion aid) and a mixture of nitric acid (70% concentration) and water. The ingredients were mixed for 8 min at the low speed setting. The water addition was adjusted to ensure that the resulting granulated material was consistent enough to be extruded. Extrusion was performed using a 4" Bonnet single screw extruder with a screw rotational speed of 20 rpm through a die fitted with quadrulobe buttons in order to achieve a 0.05" average diameter. The extrudates were dried overnight at 120° C. in a convection oven and finally calcined in a rotary calciner (6" internal diameter, four zones, 4 rpm rotational speed) at 900° C. with a feed rate of 129 g/min with an air flow of 3-4 L/min. The resulting catalyst was designated as Catalyst E and had a surface area of 396 $m^2/g$ and a $N_2$ pore volume of 0.69 cc/g.

Preparation of Catalyst F

Catalyst F was prepared as follows. 50 g of alumina in quadrulobe extrudate form with an average diameter of 0.05", a SA of 167 $m^2/g$ and a $N_2$ pore volume of 0.68 cc/g was used as the support in an incipient-wetness impregnation. 1.3 g Zr acetate hydroxide was dissolved in 34 cc of water (equivalent to the pore volume of the support). This Zr-containing solution was added drop-wise to the support as it was tumbled in an impregnation vessel consisting of rotating tilted cylindrical beaker. The tumbling of the impregnated support was then continued for an additional 30 minutes. The impregnated material was then dried overnight in air at 120° C. and finally calcined in air at 550° C. for 2 h. The resulting catalyst by analysis had $ZrO_2$ content of 1.5 wt %, SA of 143 $m^2/g$ and $N_2$ pore volume of 0.65 cc/g.

Preparation of Catalyst G

Catalyst G was prepared as follows. 50 g of a silica alumina extrudate support (from Grace containing 25 wt % alumina, 75 wt % silica) with surface area (SA) of 320 and pore volume (PV) of 0.86 cc/g, was used as the support in a 2-step incipient-wetness impregnation process. In step 1, 2 g of $La(NO_3)_3$-$6H_2O$ was dissolved in 43 cc of water and sprayed onto the tumbling support similarly to what was used to make Catalyst F, followed by 10 minutes additional residence time in the tumbling vessel. After drying the impregnated catalyst at 120° C., the second impregnation step was similarly applied using 15 g of a zirconyl nitrate solution with Zr concentration equivalent to 20 wt % $ZrO_2$. After a second 120° C. drying step and calcination in air at 550° C. for 2 hrs, this finished material had $La_2O_3$ content of 1.4 wt %, $ZrO_2$ content of 5.8 wt %, SA of 240 $m^2/g$, and $N_2$ pore volume of 0.78 cc/g.

Evaluation of Catalysts D Through G for Biodiesel Purification

The performance evaluation of Catalysts D through G for biodiesel purification was conducted in a fixed bed microreactor using the same protocol as those for Tests 1-3 except that the conditions used were as follows: temperatures in the 180-230° C. range, pressure of 70-110 psi and a Liquid Hourly Space Velocity (LHSV) of 1.0 $h^{-1}$. The biodiesel sample used for the experiments was a soy oil-based biodiesel obtained from a commercial facility containing either 0.42 wt % or 0.67 wt % monoglycerides. The tests were conducted to evaluate the performance of these catalysts for biodiesel purification at two different stages of the biodiesel manufacturing process: Process 1: After the methanol removal and optional filtration steps—with methanol addition to the biodiesel containing very little water (See FIG. 1), and Process 2: After the neutralization/washing steps performed right after the transesterification—this biodiesel sample will contain residual amounts of methanol and water (ranging from 0.2 to 2 wt %) (See FIG. 2). To simulate Process 1 the final filtered biodiesel sample was spiked only with methanol to the required level (1-2 wt %). To simulate Process 2, the final filtered biodiesel was spiked with methanol and water to achieve a total weight of 1-2 wt % methanol and 0.2 wt % water respectively. In addition tests were also conducted with a biodiesel taken after the water washing step from a commercial facility that contained methanol and water. The product collection and analyses were identical to those used for Tests 1-3.

Test 4

Evaluation of Catalyst D for Process 1

The fixed bed reactor test was carried out with the same procedure as above but with the final filtered biodiesel spiked with 1 wt % methanol and no water to simulate Process 1. The initial monoglyceride and diglyceride contents for the feed blend as measured prior to the run were 0.54 wt % and 0.13 wt % respectively. The reaction conditions used were: total pressure of 90 psi, temperature of 180° C., and LHSV of 1 $h^{-1}$ and the test was carried out for a total duration of 24 h at this condition. The results are summarized in Table 3 below. It can be observed that Catalyst D exhibits a monoglyceride reduction of 80% over this timeframe with a minimal increase in the diglyceride content.

TABLE 3

| Time on Stream (h) | Monoglycerides (wt %) | Diglycerides (wt %) |
|---|---|---|
| Initial | 0.54 | 0.13 |
| 6 | 0.04 | 0.19 |
| 15 | 0.12 | 0.23 |
| 24 | 0.11 | 0.22 |

Test 5

Evaluation of Catalyst D for Process 2

The fixed bed reactor test was carried out with the same procedure as above but with the final filtered biodiesel containing 0.42 wt % monoglycerides spiked with 2 wt % methanol and 0.2 wt % water to simulate Process 2. The initial monoglyceride and diglyceride contents for the feed blend as measured prior to the run were 0.42 wt % and 0.13 wt % respectively. The reaction conditions used were: total of pressure of 140 psi, temperature of 180° C., and LHSV of 1 h$^{-1}$ and the test was carried out for a total duration of 600 h at this condition. The results are summarized in Table 4 below. It can be observed that Catalyst D shows stable performance over this timeframe and exhibits a monoglyceride reduction of about 40% without any significant increase in the diglyceride content.

TABLE 4

| Time on Stream (h) | Monoglycerides (wt %) | Diglycerides (wt %) |
|---|---|---|
| Initial | 0.42 | 0.13 |
| 60 | 0.20 | 0.13 |
| 180 | 0.21 | 0.21 |
| 360 | 0.25 | 0.16 |
| 540 | 0.25 | 0.15 |

Test 6

Evaluation of Catalyst E for Process 1

The performance of Catalyst E for biodiesel purification was evaluated using the same protocol as discussed above with the exception that the feedstock used was the final filtered biodiesel spiked with 1 wt % methanol and no water to simulate Process 1. The initial monoglyceride and diglyceride contents for the feed blend as measured prior to the run were 0.48 wt % and 0.14 wt % respectively. The reaction conditions used were: a pressure of 90 psi, LHSV of 1 h$^{-1}$ and temperature of 180° C. The results are summarized in Table 5. It can be seen that Catalyst E decreases monoglycerides by nearly 80% with only a small portion of that contributing to diglyceride formation.

TABLE 5

| Time on Stream (h) | Monoglycerides (wt %) | Diglycerides (wt %) |
|---|---|---|
| Initial | 0.48 | 0.14 |
| 6 | 0.03 | 0.17 |
| 15 | 0.06 | 0.23 |
| 24 | 0.09 | 0.25 |

Test 7

Evaluation of Catalyst F for Process 2

The performance of Catalyst F for biodiesel purification was evaluated using the same protocol as discussed above with the exception that the feedstock used was the final filtered biodiesel spiked with 1 wt % methanol and 0.2 wt % water to simulate Process 2. The initial monoglyceride and diglyceride contents for the feed blend as measured prior to the run were 0.46 wt % and 0.15 wt % respectively. The reaction conditions used were: a pressure of 90 psi, LHSV of 1 h$^{-1}$ and temperature of 180° C. The results are summarized in Table 6. It can be seen that Catalyst F decreases monoglycerides by nearly 50% with only a small portion of that contributing to diglyceride formation. Analyses of the samples for total sterol glycosides also indicate that this catalyst reduces the level of this contaminant.

TABLE 6

| Time on Stream (h) | Monoglycerides (wt %) | Diglycerides (wt %) | Sterol Glycosides (ppm) |
|---|---|---|---|
| Initial | 0.46 | 0.15 | 9.5 |
| 6 | 0.11 | 0.29 | 5.8 |
| 60 | 0.20 | 0.31 | 5.7 |
| 78 | 0.20 | 0.29 | 6.8 |
| 90 | 0.23 | 0.32 | 5.9 |

Test 8

Evaluation of Catalyst G for Process 1

The performance of Catalyst G for biodiesel purification was evaluated using the same protocol as discussed above with the exception that the feedstock used was a final filtered biodiesel spiked with 1 wt % methanol and no water to simulate Process 1. The initial monoglyceride and diglyceride contents for the feed blend as measured prior to the run were 0.67 wt % and 0.22 wt % respectively. The reaction conditions used were: a pressure of 120 psi, LHSV of 1 h$^{-1}$ and temperature of 180° C. The results are summarized in Table 7. It can be seen that Catalyst D decreases monoglycerides by nearly 70% with only a small portion of that going to diglyceride formation.

TABLE 7

| Time on Stream (h) | Monoglycerides (wt %) | Diglycerides (wt %) |
|---|---|---|
| Initial | 0.67 | 0.22 |
| 6 | 0.20 | 0.27 |
| 15 | 0.22 | 0.28 |
| 24 | 0.22 | 0.28 |

Test 9

Effect of Methanol and Temperature on the Performance of Catalyst D for Monoglycerides and Sterol Glycosides Reduction for Process 2

The effect of methanol level and reaction temperature on the performance of Catalyst D for biodiesel purification was tested using biodiesel taken after one of the water washing steps employed in the production process, a washing step which in turn followed the transesterification and catalyst neutralization steps (simulation of Process 2). This impure biodiesel sample containing 0.4 wt % methanol and 0.2 wt % water was spiked with different levels of methanol and tested using the above fixed bed reactor protocol at different temperatures in the 180-230° C. range. As can be seen in Table 8 below, the combination of methanol and increased temperature show greater reduction in the levels of monoglycerides and sterol glycosides. In addition, this behavior with increasing temperature also demonstrates that this purification concept is catalytic.

TABLE 8

| Additional MeOH added wt % | Data at ~90 h TOS | | | Sterol glycosides (ppm) |
|---|---|---|---|---|
| | Temperature ° C. | Monoglycerides (wt %) | Diglycerides (wt %) | |
| Feed | — | 0.40 | 0.11 | 27 |
| 0 | 180 | 0.21 | 0.23 | 11 |
| 1 | 180 | 0.24 | 0.15 | 8 |
| 1.5 | 200 | 0.17 | 0.16 | <2 |
| 1.5 | 210 | 0.09 | 0.12 | <0.5 |
| 1.5 | 230 | 0.05 | 0.09 | <0.5 |

What is claimed is:

1. A process for treating a fatty acid alkyl ester-containing stream comprising impurities, and at least ninety percent by weight fatty acid alkyl ester, and optionally alcohol, the process for treating the feed stream comprising:
   (a) contacting the stream with a catalyst comprising metal oxide, wherein the metal is selected from the group of metals consisting of those in Groups 3, 4, 5, 13 and 14, and optionally, alcohol under catalytic conditions to convert the impurities in the stream to a product or by product, and
   (b) recovering a fatty acid alkyl ester stream having reduced amounts of impurities and having improved cold flow properties.

2. A process according to claim 1, comprising contacting the fatty acid alkyl ester-containing stream in (a) with a catalyst comprising mixed metal oxide of two or more metals selected from the group of metals consisting of those in Groups 3, 4, 5, 13 and 14.

3. A process according to claim 1, wherein the mixed oxide comprises magnesium oxide and alumina.

4. A process according to claim 1, wherein the mixed oxide further comprises alkaline earth aluminate spinel.

5. A process according to claim 4, wherein the alkaline earth aluminate spinel is magnesium aluminate spinel, and the catalyst further comprises rare earth oxide and an oxide of a Group 5 metal.

6. A process according to claim 5, wherein the rare earth oxide is ceria, and the Group 5 metal oxide is vanadium oxide.

7. A process according to claim 1, wherein the catalyst comprises alumina and an oxide of metal selected from the group of metals consisting of those in Groups 3, 4, 5 and 14.

8. A process according to claim 7, wherein the metal selected is zirconium.

9. A process according to claim 1, wherein the impurities are selected from the group consisting of monoglycerides, glycerin, sterol glycosides, triglycerides, diglycerides and mixtures thereof.

10. A process according to claim 1 comprising contacting the fatty acid alkyl ester-containing stream in (a) with a catalyst under catalytic conditions that comprise a temperature of at least 100° C.

11. A process according to claim 1, wherein feed stream in (a) comprises alcohol, and/or additional alcohol is contacted with said stream in (a), wherein the alcohol is selected from the group consisting of methanol, ethanol, propanol, butanol, and mixtures thereof.

12. A process comprising:
   (a) introducing triglyceride-containing feedstock and an alcohol as reactants into a reactor selected from the group consisting of continuous fixed bed reactor, a continuous tank reactor, and a batch reactor,
   (b) contacting the reactants in the reactor with a catalyst in liquid, granulated or powder form;
   (c) subjecting the feedstock and catalyst to transesterification conditions sufficient to convert triglycerides to products comprising alkyl ester derivatives of the triglycerides, and glycerin, wherein the alkyl ester derivatives of the triglycerides and impurities are present in an oil phase, wherein the oil phase comprises at least 90% by weight alkyl ester derivatives, and glycerin is present in a water soluble phase;
   (d) performing product separation to remove glycerin product from the oil phase;
   (e) contacting the oil phase separated by (d) and, optionally, any residual unreacted alcohol, with a catalyst comprising metal oxide, wherein the metal is selected from the group of metals consisting of those in Groups 3, 4, 5, 13 and 14, and, optionally, additional alcohol, under catalytic conditions to convert the impurities in the oil phase to a product or by product, and
   (f) recovering a fatty acid alkyl ester stream having reduced amounts of impurities.

13. A process according to claim 12 wherein methanol is removed from the oil phase from (d) comprising fatty acid alkyl ester, or, during the recovery of the fatty acid alkyl ester stream in (f) or wherein methanol is removed during both steps.

14. A process according to claim 12, wherein the catalyst in step (b) is a liquid homogeneous catalyst comprising soluble alkali catalyst and step (c) further comprises neutralizing the liquid catalyst prior to the separation of the oil phase in step (d).

15. A process according to claim 14, wherein the catalyst in step (b) is selected from the group consisting of alkali methoxides, alkali hydroxides, and mixtures thereof.

16. A process comprising:
   (a) introducing triglyceride-containing feedstock and an alcohol as reactants into a reactor selected from the group consisting of continuous fixed bed reactor, a continuous tank reactor, and a batch reactor,
   (b) contacting the reactants in the reactor with a catalyst in liquid, granulated or powder form;
   (c) subjecting the feedstock and catalyst to transesterification conditions sufficient to convert triglycerides to products comprising alkyl ester derivatives of the triglycerides, and glycerin, wherein the alkyl ester derivatives of the triglycerides and impurities are present in an oil phase, wherein the oil phase comprises at least 90% by weight alkyl ester derivatives, and glycerin is present in a water soluble phase;
   (d) performing product separation to remove glycerin product from the oil phase;
   (e) removing residual alcohol from the oil phase recovered in (d), (f) contacting the oil phase with adsorbent or filter, and (g) further contacting the alkyl ester-containing oil phase recovered from (f) and any impurities therein with a catalyst comprising a metal oxide, wherein the metal is selected from the group of metals consisting of Groups 3, 4, 5, 13 and 14, and, optionally alcohol, under catalytic conditions to convert impurities in the alkyl ester-containing oil phase to a product or by product, and (h) recovering a fatty acid alkyl ester stream having reduced amounts of impurities.

17. A process according to claim 16 wherein methanol is removed from the oil phase from (d) comprising fatty acid alkyl ester, or during the recovery of the fatty acid alkyl ester stream in (h) or wherein methanol is removed during both steps.

18. A process comprising:
(a) introducing triglyceride-containing feedstock and an alcohol as reactants into a reactor selected from the group consisting of continuous fixed bed reactor, a continuous tank reactor, and a batch reactor, (b) contacting the reactants in the reactor with a catalyst in liquid, granulated or powder form;

(c) subjecting the feedstock and catalyst to transesterification conditions sufficient to convert triglycerides to products comprising alkyl ester derivatives of the triglycerides, and glycerin, wherein the alkyl ester derivatives of the triglycerides, and impurities are present in an oil phase, and glycerin is present in a water soluble phase;

(d) performing product separation to remove glycerin product from the oil phase;

(e) subjecting the oil phase to further transesterification in one or more reactors with additional alcohol under conditions sufficient to convert triglycerides, diglycerides and monoglycerides to products comprising alkyl ester derivatives of and optionally glycerin;

(f) recovering the alkyl ester derivatives in an oil phase with one or more product separation steps; and (g) contacting the recovered oil phase comprising at least 90% alkyl ester derivatives, and any impurities therein and unreacted alcohol, with a catalyst comprising a metal oxide, wherein the metal is selected from the group of metals consisting of those in Groups 3, 4, 5, 13 and 14, and, optionally, additional alcohol, under catalytic conditions to convert the impurities in the recovered oil phase to a product or by product, and (h) recovering a fatty acid alkyl ester stream having reduced amounts of impurities.

19. A process according to claim 18, comprising contacting the recovered oil phase with a catalyst comprising mixed oxide.

20. A process according to claim 18, wherein the catalyst contacting the recovered oil phase comprises magnesium oxide and alumina.

21. A process according to claim 18, wherein catalyst contacting the recovered oil phase comprises mixed oxide that further comprises alkaline earth aluminate spinel, rare earth oxide, and an oxide of a Group 5 metal.

22. A process according to claim 21, wherein the rare earth oxide is cerin, and the Group 5 metal oxide is vanadium oxide.

23. A process according to claim 18 wherein the catalyst contacting the recovered oil phase comprises alumina and an oxide of metal selected from the group of metals consisting of those in Groups 3, 4, 5 and 14.

24. A process according to claim 18, wherein the impurities comprise glycerin, sterol glycosides, and/or triglyceride, diglyceride and/or monoglyceride.

25. A process according to claim 18 comprising contacting the recovered oil phase with a catalyst under catalytic conditions comprising a temperature of at least 100° C.

26. A process according to claim 18, wherein the recovered fatty acid alkyl ester stream has properties such that the ester meets the cold flow specification for use as a biodiesel fuel such as the ASTM method D7501.

27. A process according to claim 21, wherein the alkaline earth aluminate spinel is magnesium aluminate spinel.

28. A process according to claim 18, wherein the catalyst in (b) is an alkali catalyst.

29. A process according to claim 17, wherein methanol is removed during the recovery of the fatty acid alkyl ester stream in (h).

30. A process according to claim 1, wherein the catalyst in (a) comprises alumina.

31. A process according to claim 18 wherein the catalyst contacting the recovered oil phase comprises alumina.

32. A process according to claim 12, comprising contacting the oil phase with a catalyst comprising mixed oxide.

33. A process according to claim 12, wherein the catalyst contacting the oil phase comprises magnesium oxide and alumina.

34. A process according to claim 12, wherein catalyst contacting the oil phase comprises mixed oxide that further comprises alkaline earth aluminate spinel, rare earth oxide, and an oxide of a Group 5 metal.

35. A process according to claim 34, wherein the rare earth oxide is ceria, and the Group 5 metal oxide is vanadium oxide.

36. A process according to claim 12, wherein the impurities comprise glycerin, sterol glycosides, and/or triglyceride, diglyceride and/or monoglyceride.

37. A process according to claim 12 comprising contacting the oil phase with a catalyst under catalytic conditions comprising a temperature of at least 100° C.

38. A process according to claim 12, wherein the recovered fatty acid alkyl ester stream has properties such that the ester meets the cold flow specification for use as a biodiesel fuel such as the ASTM method D7501.

39. A process according to claim 34, wherein the alkaline earth aluminate spinel is magnesium aluminate spinel.

40. A process according to claim 12 wherein the catalyst contacting the oil phase comprises alumina.

41. A process according to claim 16, comprising contacting the recovered oil phase in (g) with a catalyst comprising mixed oxide.

42. A process according to claim 16, wherein the catalyst contacting the recovered oil phase in (g) comprises magnesium oxide and alumina.

43. A process according to 16, wherein catalyst contacting the recovered oil phase in (g) comprises mixed oxide that further comprises alkaline earth aluminate spinel, rare earth oxide, and an oxide of a Group 5 metal.

44. A process according to claim 43, wherein the rare earth oxide is ceria, and the Group 5 metal oxide is vanadium oxide.

45. A process according to claim 16, wherein the impurities comprise glycerin, sterol glycosides, and/or triglyceride, diglyceride and/or monoglyceride.

46. A process according to claim 16 comprising contacting the recovered oil phase in (g) with a catalyst under catalytic conditions comprising a temperature of at least 100° C.

47. A process according to claim 16, wherein the recovered fatty acid alkyl ester in step (h) has properties such that the ester meets the cold flow specification for use as a biodiesel fuel such as the ASTM method D7501.

48. A process according to claim 43, wherein the alkaline earth aluminate spinel is magnesium aluminate spinel.

49. A process according to claim 16, wherein the catalyst in (b) is an alkali catalyst.

50. A process according to claim 16 wherein the catalyst contacting the recovered oil phase in (g) comprises alumina.

* * * * *